United States Patent
Yang

(10) Patent No.: US 9,512,397 B2
(45) Date of Patent: *Dec. 6, 2016

(54) MICRO AND NANO SCALE STRUCTURES DISPOSED IN A MATERIAL SO AS TO PRESENT MICROMETER AND NANOMETER SCALE CURVATURE AND STIFFNESS PATTERNS FOR USE IN CELL AND TISSUE CULTURING AND IN OTHER SURFACE AND INTERFACE APPLICATIONS

(71) Applicant: Shengyuan Yang, West Melbourne, FL (US)

(72) Inventor: Shengyuan Yang, West Melbourne, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/456,833

(22) Filed: Aug. 11, 2014

(65) Prior Publication Data
US 2015/0072430 A1    Mar. 12, 2015

Related U.S. Application Data

(63) Continuation-in-part of application No. 13/656,808, filed on Nov. 25, 2012, now Pat. No. 8,802,430, which
(Continued)

(51) Int. Cl.
*C12N 5/077* (2010.01)
*C12N 5/00* (2006.01)

(52) U.S. Cl.
CPC ......... *C12N 5/0068* (2013.01); *C12N 2533/12* (2013.01); *C12N 2533/30* (2013.01); *C12N 2533/52* (2013.01); *C12N 2535/10* (2013.01)

(58) Field of Classification Search
None
See application file for complete search history.

(56) References Cited

U.S. PATENT DOCUMENTS

| 7,195,913 B2 | 3/2007 | Guire |
| 2008/0057578 A1 | 3/2008 | Kuwabara |

(Continued)

OTHER PUBLICATIONS

Hwang et al., Controlled cellular orientation on PLGA microfibers with defined diameters, Biomed Microdevices (2009) 11:739-746.
(Continued)

*Primary Examiner* — Karen Cochrane Carlson
*Assistant Examiner* — Jennifer M. H. Tichy
(74) *Attorney, Agent, or Firm* — John L. DeAngelis; Beusse Wolter Sanks & Maire, PLLC.

(57) ABSTRACT

A structure for use in cell and tissue culturing and in other surface and interface applications. The structure comprises a first material layer defining one or more surface features therein disposed randomly or in a pattern, the one or more surface features having the same or different sizes and cross sectional shapes, a second material layer disposed in or on the one or more surface features, a microstructure disposed in or on the one or more surface features and at least partially embedded and immobile within the second material layer, the microstructure presenting a curvature and a stiffness value and protruding above an upper surface of the second material, a size of the microstructure between 1 nanometer and 10 millimeters, and the structure for use in cell and tissue culturing and in other surface and interface applications wherein a cell grows on the microstructure.

12 Claims, 10 Drawing Sheets

Related U.S. Application Data is a continuation-in-part of application No. 13/426,593, filed on Mar. 21, 2012, now abandoned.

(56) References Cited

U.S. PATENT DOCUMENTS

| | | |
|---|---|---|
| 2009/0197333 A1 | 8/2009 | Saito |
| 2010/0129908 A1 | 5/2010 | Fang |
| 2010/0151491 A1 | 6/2010 | Himmelhaus |
| 2010/0330644 A1 | 12/2010 | Feinberg |

OTHER PUBLICATIONS

James et al., Subcellular Curvature at the Perimeter of Micropatterned Cells Influences Lamellipodial Distribution and Cell Polarity, Cell Motility and the Cytoskeleton 65: 841-852 (2008).

Rumpler et al., The effect of geometry on three-dimensional tissue growth, J. R. Soc. Interface (2008) 5, pp. 1173-1180.

Smeal et al., Substrate Curvature Influences the Direction of Nerve Outgrowth, Annals of Biomedical Engineering, vol. 33, No. 3, Mar. 2005, pp. 376-382.

Kang et al., Porous Poly(Lactic-Co-Glycolic Acid) Microsphere as Cell Culture Substrate and Cell Transplantation Vehicle for Adipose Tissue Engineering, Tissue Engineering: Part C vol. 14, No. 1, 2008.

Wang, et al, "Preparation of a Flexible, Porous Polyacrylamide Substrate for Mechanical Studies of Cultured Cells", Methods in Enzymology, vol. 298, p. 489-496, 1998.

Damlijanovic, et al, Bulk and Mircropatterned Conjugation of Extracellular Matrix Proteins to Characterized Polyacrylamide Substrates for Cell Mechanotransduction Assays:, Bio Techniques, vol. 39, No. 6 pp. 847-851.

Engler, et al, "Surface Probe Measurements of the Elasticity of Sectioned Tissue, Thin Gels and Polyelectrolyte Multilayer Films: Correlations Between Substrate Stiffness and Cell Adhesion", Surface Science 570, p. 142-159.

Yang, et al. Micromachined Force Sensors for the Study of Cell Mechanics, American Institute of Physics, Review of Scientific Instruments, p. 044307-044307.8. 2005.

MICRO AND NANO SCALE STRUCTURES DISPOSED IN A MATERIAL SO AS TO PRESENT MICROMETER AND NANOMETER SCALE CURVATURE AND STIFFNESS PATTERNS FOR USE IN CELL AND TISSUE CULTURING AND IN OTHER SURFACE AND INTERFACE APPLICATIONS

REFERENCE TO RELATED APPLICATIONS

The present application is a continuation-in-part application of application Ser. No. 13/656,808 filed on Nov. 25, 2012, now U.S. Pat. No. 8,802,430 issued on Aug. 12, 2014, which is a continuation-in-part application of application Ser. No. 13/426,593 filed on Mar. 21, 2012, both applications are incorporated by reference herein in their entirety.

FIELD OF THE INVENTION

The present invention is directed generally to micro and nano scale structures disposed in a material to present micrometer and nanometer scale local curvature and stiffness configurations and curvature and stiffness patterns for use in cell and tissue culturing and in other surface and interface applications.

BACKGROUND OF THE INVENTION

Cells survive in a mechanical environment of a tissue that the cells are part of. It has been shown that cell behaviors are extremely sensitive to the stiffness of the material on which the cells grow. For example, cell growth and movement can be guided solely by the rigidity or stiffness of a material layer where epithelial cell traction forces are proportional to material layer rigidity; matrix elasticity directs stem cell lineage specification; on microstructured anisotropic material layers, epithelial cells migrate along the direction of greatest stiffness; within a range of stiffness values spanning that of soft tissues, fibroblasts tune their internal stiffness to match that of their material layer.

Studies of interactions between cells and their surrounding environments have been receiving increased attention over the past twenty years. The results of several such studies are summarized below. Cell-substrate interactions can profoundly affect cell behavior, including adhesion, spreading, migration, division, differentiation, apoptosis, and internal cellular signaling. The binding interactions between cells and their material layer(s) are influenced by mechanical stimuli such as material stiffness and material curvatures. The effects of material stiffness on cell behaviors have been extensively studied. However, the effects of material curvatures are not well documented. Since the materials on which the cells grow in vivo are normally not flat, the responses of cells to material curvatures should also be a fundamental aspect of cell mechanosensitivity and mechanotransduction. The importance of material curvature effects on cell behaviors can be illustrated by understanding the process of cell attachment and growth on curved surfaces of bones and implants in vivo.

In 1952, researchers Weiss and Garper used the term "contact guidance" to describe the orientation of cell locomotion in response to the topographic structures of the material on which the cell grows. In 1976, by culturing chick heart fibroblasts on convex cylindrical glass fibers, researchers Dunn and Heath demonstrated that cells respond to material curvatures when the radii of the curvatures are comparable to the cell sizes, and they fitted a radius of curvature of 100 micrometers above which the curvature effects on cell behavior were negligible.

Dunn and Ebendal showed that contact guidance on aligned collagen gels is largely a response to the three-dimensional shape of the material. By comparing normal and virally transformed hamster cells, Fisher and Tickle illustrated that the organization of microfilaments plays a role in determining the orientation of cells on curved surfaces.

Smeal et al. determined that curvature was sufficient to influence the directional outgrowth of nerve cells by culturing nerve cells on filamentous surfaces and measuring directional growth. They found that the mean direction of neurite outgrowth aligned with the direction of minimum principal curvature, and the spatial variance in outgrowth direction was directly related to the maximum principal curvature. Maduram et al. established dependence between cell polarity and shape by noting the presence of small molecules that alter actomyosin contractility. This finding revealed a stronger dependence on contractility for shapes having straight edges in contrast to those having curved edges.

Rumpler et al. investigated the role of curvature on the growth of tissues. They reported that the local rate of the tissue formed by osteoblasts is strongly influenced by the geometrical features of the channels in an artificial three-dimensional matrix. Curvature-driven effects and mechanical forces within the tissue explained the growth patterns as demonstrated by numerical simulation and confocal laser scanning microscopy. Hwang et al. investigated the effects of microfiber diameter on the orientation of adhered cells. For this purpose, mouse fibroblast L929 cells were cultured on the surface of poly (D,L-lactic-co-glycolic acid) (PLGA) fibers of defined diameters ranging from 10 to 242 microns, and their adhesion and alignment were quantitatively analyzed. They found that the mean orientation of cells and the spatial variation of the cell alignment angle directly related to the microfiber diameter. Cells cultured on microfibrous scaffolds oriented along the long axis of the microfiber. An increase in cellular orientation along the longitudinal direction was noted as fiber diameter decreased.

Sanz-Herrera et al. proposed a cell constitutive model to mathematically simulate cell attachment on curved surfaces activated by contractile forces. They analyzed a single fiber bundle composed of microtubules and actin filaments activated by actomyo sin motors. Then the model was macroscopically extended to the cytoskeletal level using homogenization.

In the above-mentioned literature, curvature effects on cell behaviors were studied by experiments using glass rods or polymer fibers. To date, there is no reported experimental study on curvature effects of spherical materials or microstructures on cell behaviors, which motivated research by the present inventor and lead to the development of the described invention.

BRIEF DESCRIPTION OF THE DRAWINGS

The features of this invention will be apparent from the following description of the invention, as illustrated in the accompanying drawings, in which like reference characters refer to the same parts throughout the different figures.

DETAILED DESCRIPTION OF THE INVENTION

Figure 1:
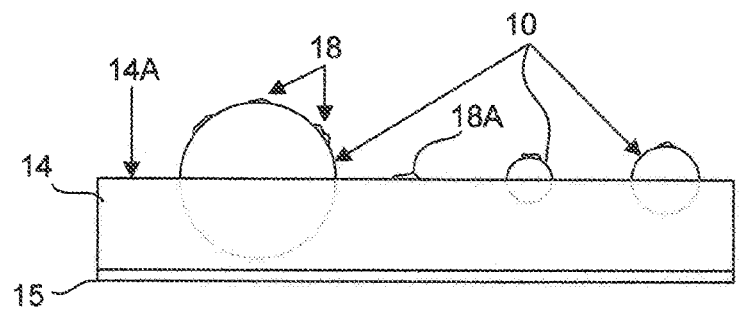
FIGS. 1-4 illustrate various embodiments of microstructures embedded in various material layers.

Before describing in detail the particular micro and nano scale structures disposed in or above a material layer in accordance with the present invention, it should be observed that the present invention resides primarily in a novel combination of elements and method steps. Accordingly, these elements have been represented by conventional elements in the drawings, showing only those specific details that are pertinent to the present invention so as not to obscure the disclosure with structural details that will be readily apparent to those skilled in the art having the benefit of the description herein.

The following embodiments are not intended to define limits as to the structure or methods of the invention but only to provide exemplary constructions. The described embodiments are permissive rather than mandatory and illustrative rather than exhaustive.

One embodiment the present invention teaches a polyacrylamide (PA) gel embedded with micro glass balls of various diameters to study cell mechanobiological responses to curvatures, stiffness values, patterns of various curvatures and stiffness values and other surface interface parameters. In one application the inventor cultured NIH-3T3 mouse fibroblasts on glass balls having diameters ranging from about 5 micrometers to about 2 millimeters, and analyzed the cell morphologies by using an optical microscope and a 3D confocal laser scanning microscope. The inventor found that the fibroblasts are sensitive to the curvatures of the balls, and there are significant differences in the attachment rates, migration speeds, and morphologies for cells cultured on glass balls of diameters at or below about 500 micrometers. The inventor also observed the cell spreading responses to the local stiffness effect of the glass balls, and compared the cell migration behavior on cylindrical glass tubes with similar diameters to the glass balls.

The microstructures for use in the various described embodiments and applications can exhibit any of the following shapes: ball-like, spherical, elliptical and cylindrical. Any other defined or random shapes can also be employed. The microstructures can also be solid or hollow, such as a spherical shell. In certain embodiments the microstructures comprise glass balls. The curves or shape of the microstructures can be controlled to provide any predetermined curvature or the microstructures can be formed to exhibit random curves and/or random shapes. Certain structural shapes are also described in the related patent application referred to above, i.e., application Ser. No. 13/426,593.

In certain embodiments the microstructures have defined curvature and/or stiffness values. In certain embodiments and applications these values may be random, while in other embodiments and applications the values are not random but instead are defined based on the experiment in which they are to be utilized. Whether random or defined, the microstructures are fabricated according to these parameters then loaded into or onto a material layer for use in cell or tissue culturing and in other surface and interface applications.

In the various described embodiments, the microstructures can range in size from about 1 nanometer to about 10 millimeters, presenting micro-and nano-interfaces between the material layer and the cells.

Figure 5:
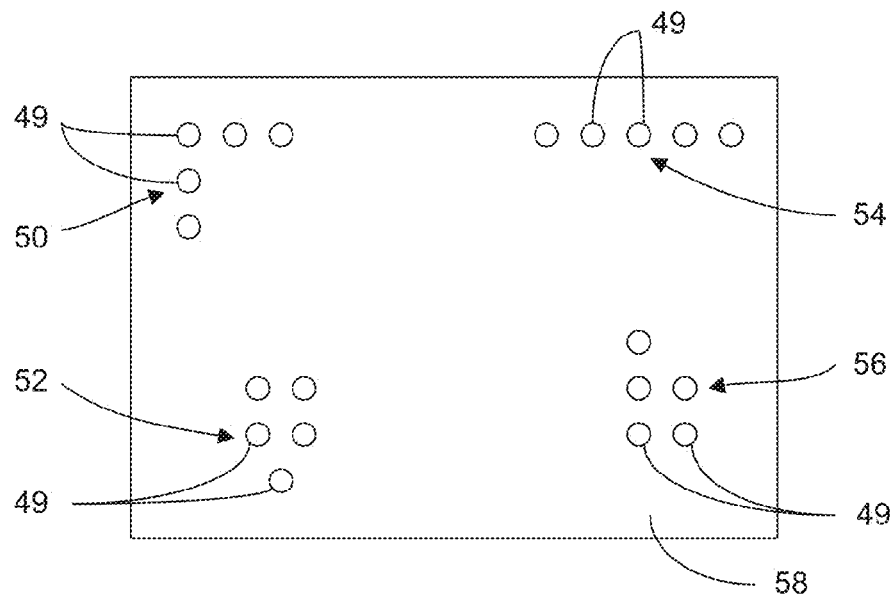
FIG. 5 illustrates different clusters of microstructures.

The shaped microstructures, whether all having the same shape or different shapes and whether all have the same size or different sizes and the same stiffness value or different stiffness values, can be disposed within a gel or another material layer, to provide various shapes, shape patterns, curvatures, curvature patterns and stiffness patterns for cell and tissue culturing and for use in other surface and interface applications. The stiffness patterns and shapes can be predetermined by an ordered placement (e.g., uniform, periodic or symmetrical) of the microstructures or the microstructures can be randomly distributed within the gel or another material layer to provide random shapes and random stiffness patterns. Both the ordered and random placement of the stiffness values and microstructure shapes and sizes within the gel or another material layer are important for use in cell and tissue culturing and in other surface and interface applications. Microstructures 49, see FIG. 5, can be disposed in a single pattern within the gel or another material layer or can be disposed in clusters of several different patterns 50, 52, 54, and 56 across the surface of a gel 58 as shown in FIG. 5. In lieu of patterned arrangements, the microstructures 49 can be placed randomly within the surface of the gel 58.

A material of the microstructures comprises plastic, glass, silicon, or silicon nitride or any other material suitable for use in cell and tissue culturing or in any other surface interface applications. Any other materials that will permit the culturing of cells thereon, i.e., the material should preferably exhibit a curvature (convex or concave, be able to change its shape in situ) and be able to retain that curvature during cell/tissue culturing can also be used. Also, all the microstructures (i.e., regions having certain stiffness values) used in any one cell culturing experiment do not need to comprise the same material, the same shape, nor the same stiffness value.

The use of a gel for embedding the shaped microstructures is not required according to the invention. Any material layer can be used if it exhibits properties sufficient for receiving and retaining the microstructures, such as relatively soft or deformable but yet sufficiently rigid to retain the microstructures in place during cell/tissue culturing. For example, in lieu of the gel 58 of FIG. 5 the material layer may comprise any other material such as glass, plastic, silica, silicon, silicon nitride, composite materials, transparent materials, non-transparent materials, or any other material suitable for use as the material layer in cell and tissue culturing or in any other surface interface applications.

Preparation of Gel for the Material Layer

The protocol used to prepare the PA gels for use in certain embodiments of the present invention is described below. According to one embodiment a 40% w/v (weight/volume) acrylamide stock solution is prepared by mixing 40 g of acrylamide powder (available from Fisher-Biotech, Pittsburgh, Pa., CAS no. 79061) with 100 milliliters of deionized $H_2O$. A 2% w/v bis-acrylamide stock solution is prepared by mixing 1 gram bis-acrylamide powder (available from Fisher-Biotech, Pittsburgh, Pa., CAS no. 110269) with 50 milliliters deionized $H_2O$. Final volumes of 1000 microliters of PA solutions are prepared by mixing the acrylamide stock solution at final concentrations of 3% to 8% w/v with the bis-acrylamide stock solution at final concentration of 0.02% to 0.1% w/v. To polymerize the PA solutions, 1.5 microliters of N,N,N',N-tetramethylethylenediamine (TEMED) (available from Fisher-Biotech, Pittsburgh, Pa., CAS no. 110189) and 5 microliters of 10% w/v ammonium persulfate are added to the mixed PA solution.

A fixed volume of 100 microliters of the PA solution is pipetted onto the center of a 30 millimeter diameter cell culture dish. Depending on the desired studies, appropriate numbers or a combination of glass balls with diameters of about 2 millimeters, 1.1 millimeters, 900 micrometers 750 micrometers, 500 micrometers, mixed 50-300 micrometers, and mixed 5-100 micrometers (available from Blockhead stamps of Portland, Oreg.) are immediately dropped onto the PA solution. To evenly press the glass balls into the unpolymerized gel, a 22 millimeter diameter cover slip is then carefully placed on top of the PA solution. The polymerization process is completed in about 24 hours and then the top cover slip is slowly peeled off. The glass ball embedded PA gel, which is attached to the cell culture dish, is soaked with 5 milliliters PBS for about three days.

PA gels with a wide range of elastic moduli, E, can be prepared using the concentration scheme described above. The most flexible gel with 3% w/v acrylamide and 0.10% w/v bis-acrylamide has an elastic modulus (E) of 1 kPa, while the stiffest gel with 8% w/v acrylamide and 0.08% w/v bis-acrylamide yields an E of 75 kPa. In addition, the intermediate gel with 8% w/v acrylamide and 0.02% w/v bisacrylamide has an E of 10 kPa.

Since cultured cells adhere poorly to the PA surface, the inventor coated the gels with adhesion molecules to provide a physiological adhesive surface for the cell culture. The inventor coated a fibronectin-like engineering protein (available from Sigma-Aldrich of St. Louis, Mo., no. F8141-1MG) on the glass ball embedded PA gel surface and then these gels were left at room temperature for about 24 hours before plating cells.

In addition, the inventor also prepared cylindrical glass tubes (available from Fisher Scientific of Atlanta, Ga., No. 212011A) having diameters similar to the diameters of the glass balls. In one embodiment the diameters of the cylindrical glass tubes are 2 millimeters, 1.09 millimeters, 930 micrometers, 760 micrometers, 530 micrometers, and 460 micrometers. Both ends of the cylindrical glass tubes are fixed on the bottom of cell culture dish by using 75 kPa PA gels to prevent any sliding or rolling of the cylindrical glass tubes.

Cell Culturing According to One Embodiment

NIH-3T3 mouse fibroblasts were cultured in Dulbecco's Modified Eagle Medium (available from ATCC of Manassas, Va., no. 30-2002) with 4500 milligrams/liter glucose, 4 millimoles/liter-glutamine, 1 millimole sodium pyruvate, and 1500 milligram/liter sodium bicarbonate, 10% calf bovine serum (available from ATCC of Manassas, Va., No. 30-2030), and 1% penicillin-streptomycin (available from MP Biomedicals of Solon, Ohio, No. 091670049). The cells were incubated at 37° C. with a humidified 5% $CO_2$ atmosphere and the culture medium was changed twice per week.

Cell Staining and Confocal Microscopy

To obtain three-dimensional (3D) images of cells on curved surfaces, the inventor used a confocal laser scanning microscope (available from Nikon Instruments Inc. of Melville, N.Y., Eclipse 90i). For confocal microscopy, the cells were directly treated using a membrane probe, N-(3-Triethylammoniumpropyl)-4-(4-(Dibutylamino)styryl) Pyridinium Dibromide (available from FM of Carlsbad, Calif., 1-43 invitrogen no. T3163), through 5 micrograms/milliliter diluted in ice-cold Hanks' balanced salt solution (HBSS) (available from Invitrogen of Carlsbad, Calif., no. 14175079).

A. Glass Ball Embedded in PA Gel Platform

A class of PA gels with glass balls embedded with diameters of 2 millimeters 1.1 millimeters, 900 micrometers, 750 micrometers, 500 micrometers, mixed 50-300 micrometers, and mixed 5-100 micrometers were prepared using the protocol described above. FIG. 1 illustrates microstructures 10 embedded in a PA gel platform 14 for use in tissue and cell culturing and in other surface and interface applications. The PA gel platform is disposed on a material layer 15. In this platform, some cells 18 reside on the top of the microstructures 10 while other cells 18A live on a surface 14A of the PA gel platform 14.

The extent to which the microstructures are embedded in the gel can be randomly determined, for example, by simply dropping the microstructures onto an exposed surface of the gel. In another embodiment the microstructures can be disposed such that an equal volume of each microstructure extends above the gel surface 14A or each microstructure extends an equal distance above the gel surface 14A.

The gel platform 14 functions as both a soft material layer and an adhesive surface to prevent any sliding or rolling of the glass balls 10. As can be seen in a scanning electron microscope (SEM) image of this platform (not shown) glass balls of 900 micrometers diameter, 500 micrometers diameter, and below 300 micrometers diameters extend out from an upper surface of the PA gel platform 14. Because the microstructures float on top of the PA gel platform prior to polymerization, the tops of the microstructures may be bare or have a thin coating of the PA gel material.

Figure 2:
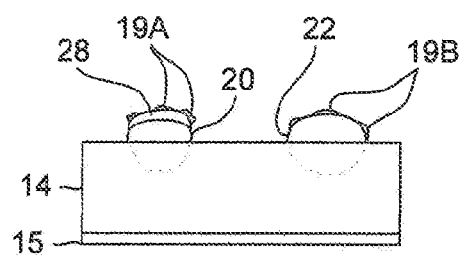

FIG. 2 illustrates microstructures 20 and 22 disposed in the PA gel platform 14. An additional layer of gel material 28 is disposed on the microstructure 20 and the cells 19A grow on the gel material 28. The cells 19B grow directly on the microstructure 22 with no intervening layer of gel material.

Figure 3:
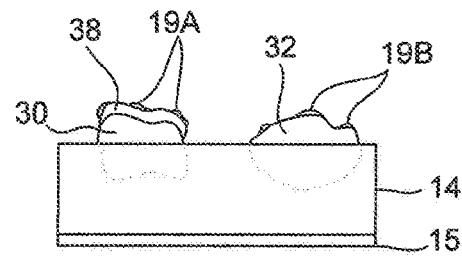

FIG. 3 illustrates differently-shaped microstructures 30 and 32 disposed in the PA gel platform 14. An additional layer of gel material 38 is disposed on the microstructure 30 and the cells 19A grow on the gel material 38. The cells 19B grow directly on the microstructure 32 with no intervening layer of gel material.

Figure 4:
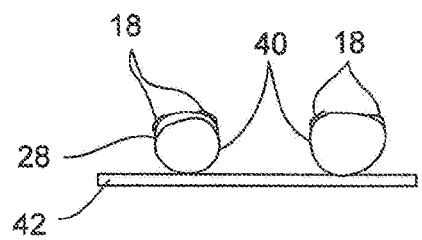

FIG. 4 illustrates an embodiment without the gel platform layer. In this embodiment the microstructures 40 are disposed on a material layer 42. An adhesive material (not shown) affixes the microstructures 40 to the material layer 42.

The inventor has compared the cells cultured on the PA gel material, cells cultured on the glass ball microstructures with a thin coating of PA gel material, and cells cultured on bare glass ball microstructures. He has determined that the cells cultured on these three surfaces have different morphologies. Within 24 hours in culture, cells on bare glass balls formed a few long narrow lamellipodia to spread and migrate, but cells on PA gels and cells on glass balls with a thin coating of PA did not form lamellipodia.

The surfaces of the glass balls may not be smooth. In one embodiment the 150 micrometer and 500 micrometer diameter glass balls were less rough than the 2 millimeter diameter glass ball. It has been shown that nano-scale surface roughness affects cell morphology, proliferation, and immunophenotype. However, here the inventor did not consider the effect of nano-scale topography.

Effects of Material Layer Curvature on Fibroblast Morphology

After 24 hour in culture, the NIH-3T3 fibroblasts on the 2 millimeter diameter glass ball were very well spread. These fibroblasts were almost indistinguishable from those grown on flat glass. The cells on both the flat glass and 2 millimeter diameter glass ball were very well spread and had two or three lamellipodia for active migration. Also, for both surfaces, the formation of some small clusters of cells was noted. This means the cells migrated actively to connect with each other and cellular division began occurring at this time. The cells on the 2 millimeter diameter glass ball were slightly less spread than the cells on the flat glass although both the cells on the flat glass and the cells on the 2 millimeter diameter glass ball had similar morphologies and behaviors. It was evident that the cells can recognize large radii of curvature such as 2 millimeter diameter glass balls.

The cells on the 1.1 millimeter, 900 micrometer, and 750 micrometer diameter glass balls had the similar cell shapes. The cells were less spread compared to those on the flat glass and 2 millimeter diameter glass ball. While some cells still had a round shape with two short lamellipodia after 24 hours in culture, the majority of the cells had a more spread shape.

On the other hand, the cells on a 500 micrometer diameter glass ball had different cell shapes compared to the cells on larger balls. The round cells were dominant and some cells formed a long narrow lamellipodium while still being round. Although these cells did not spread and migrate actively, the inventor observed that they grew minimally and retained their round shape after 48 hours in culture.

The cells placed on the 154 micrometer and 68 micrometer diameter glass balls closely resembled the cells on the 500 micrometer diameter glass ball, which were round-shaped with one or two lamellipodia.

Confocal Laser Scanning Microscopy

Confocal microscope images of two NIH-3T3 fibroblasts on a flat glass and on a 900 micrometer diameter glass ball were also recorded. The fibroblast on the flat glass was very well spread and had many filopodia. The height of this fibroblast was measured to be 8 micrometers along a YZ axis view. The fibroblast maintained a round shape with two long narrow lamellipodia.

Cell Spreading Behaviors Due to the Effect of Local Material Layer and Microstructure Stiffness It is well known by those skilled in the art that cell spreading depends on material layer and microstructure stiffness. Cells generate more traction force and develop a broader and flatter morphology on stiffer material layers than they do on softer but equally adhesive material layers. Cells preferentially migrate from a soft to a hard surface. Normal NIH-3T3 cells, for instance, undergo more apoptosis and less proliferation on soft as opposed to stiff material layers. Most cell types studied spread more and adhere better to harder substrates, and some cannot grow on very soft (<50 Pascals) surfaces. In the inventor's experiments, he found that on the 75 kiloPascals pure PA gels, NIH-3T3 cells spread well and migrated actively. The inventor made 75 kiloPascal gels embedded with diameters of mixed 5-100 micrometers microstructures or glass balls. A round cell was formed on two glass balls with the cell wrapped over the two glass balls. This cell grew and spread over the two glass balls. Cells placed on very small glass balls with diameters smaller than about 20 micrometers did not spread and migrate. They maintained a round shape while growing on the balls and then similarly wrapped over the small glass balls. They also lived on the balls because the glass balls were stiffer than the 75 kiloPascal gel. It was observed that cells on the 75 kiloPascal gel were still moving actively while cells on the small glass balls were still wrapped over the glass ball after 96 hours in culture.

The inventor also found NIH-3T3 fibroblasts cannot attach and spread on 10 kiloPascal PA gels. Even when the inventor attached cells on the surface of the 10 kiloPascal gels with fibronectin coating, the attached cells still did not spread. However, fibroblasts could spread when there were very small stiff particles near the cells. Some cells stretched over two small glass balls with diameters smaller than 30 micrometers, while other cells located on the surface of the 10 kiloPascal gel were still round. The cell extended two lamellipodia to the glass balls and the ends of the two lamellipodia stuck to the two glass balls, respectively. This observation shows that the cell spreading behaviors respond to local material layer and microstructure stiffness values.

Cell Migration on Both Spherical and Cylindrical Surfaces

The inventor observed cell migration behaviors on both the glass balls and the cylindrical glass tubes with various diameters. Cell movements on a glass ball with a diameter of 500 micrometers and movements on a cylindrical glass tube with a diameter of 440 micrometers were observed. On the glass ball, a round cell with two long narrow lamellipodia migrated without directivity on the surface of the ball for 48 hours in culture. On the cylindrical glass tube, after 6 hours in culture, a narrow and long fibroblast was observed on the center surface of the glass tube angled at about 45 degrees to the longitudinal direction of the glass tube. After 12 hours in culture, this cell shortened in length and rotated by about 10 degrees to the longitudinal direction of the tube. This cell shortened again and aligned itself parallel to the longitudinal direction of the tube after 24 hours in culture. This fibroblast became round and moved in the opposite direction after 48 hours in culture. Therefore the cell on the cylindrical glass tube tended to align to the longitudinal direction of the tube while the cell on the glass ball migrated irregularly. Both of the cells showed poor motilities and growth rates for 48 hours in culture.

The cell spread area was measured for a number of randomly selected cells ($n_{total}$=95). In general, the mean cell spread area decreased with the decreasing of the glass ball diameter, from flat glass plates to large balls to small balls. The smallest cell spread area, 209 micrometers$^2$, was found on a 63 micrometers diameter glass ball, and the maximal average cell spread area, 1592 micrometers, was clearly obtained with flat glass plates. The smallest glass ball to which a fibroblast adhered without wrapping over the glass ball was 58 micrometers in diameter. The cell spread area increased as a function of the ball diameter with three different slopes in the three distinct regions depending on the ball diameters. In a Region 1 cells grew on 50-300 micrometers diameter glass balls, and the cell spread area, as a function of the ball diameter, fitted a linear relationship ($n_{Region\ 1}$=35) with the largest slope compared to those of Region 2 and Region 3. In Region 2, cells grew on 500-900 micrometer diameter glass balls, the mean cell spread area had a linear trend ($n_{Region\ 2}$=30) as a function of the ball diameter, but the slope was approximately 24% of the slope for Region 1. In Region 3, cells grew on 1.1 millimeter diameter glass balls, 2 millimeters diameter glass balls, and to flat glass, the mean cell spread area increased with the increase of the ball diameter, and the slope between data points of the 1.1 millimeter diameter glass balls and 2 millimeter diameter glass balls was similar to that of Region 2 ($n_{Region\ 3}$=30). From 900 micrometers diameter to 1.1 millimeters diameter glass balls, there was a 50% sudden rise in the mean cell spread area. The mean comparison of one-way analysis of variance (ANOVA) with the Tukey and Dunnett C post-test indicated that the mean cell spread area for each diameter of the glass balls significantly differ from each other at the 0.01 level of significance.

The fibroblasts showed lower attachment rates and migration speeds when the diameter of the glass balls decreased. For glass balls of diameters at or below 500 micrometers the fibro-blasts had very low attachment rates and migration speeds for larger glass balls. Thus, although the fibroblasts can easily attach the surfaces of glass balls with large radii, such as flat glass plates and 2 millimeter diameter glass balls, it is hard for them to adhere to the surfaces of glass balls with small radii or curvatures, such as below 500 micrometer diameter glass balls. In addition, the cells growing on glass balls of diameters at or below 500 micrometers showed higher aspect ratios compared to those growing on glass balls of larger diameters. Therefore, the inventor concluded that the attachment, spreading, migration behaviors of the NIH-3T3 fibroblasts are sensitive to the material layer and microstructure curvatures and these behaviors for cells growing on material layers and microstructures with diameters at or below 500 micrometers are significantly different from those for cells growing on material layers and microstructures with larger diameters.

In summary, micro glass balls (microstructures) embedded in PA gels were developed to study cell mechanobiological responses to material layer curvatures. NIH-3T3 mouse fibroblasts were cultured on these material layers with glass balls ranging in diameters from 5 micrometers to 2 millimeters, and morphologies of cells growing on glass balls were analyzed by an optical microscope and a 3D confocal laser scanning microscope. The curvature of the surface to which a cell adheres has profound effects on cell attachment, migration, and morphology. Fibroblasts showed lower spread areas and migration speeds as the diameter of the glass ball decreased, and showed poor growth rates and motilities both on glass balls and on cylindrical glass tubes with diameters at or less than about 500 micrometers. Cell spreading behavior responded to the local stiffness effect induced by the glass balls in the gels. Experiments showed that the cells did not spread on a stiff gel but wrapped over the small glass balls, and the cells spread on a soft gel by attaching to the two small separate glass balls. When a cell attaches to a curved surface, it creates a distortion on the cell cytoskeleton, and then the cell does not work in an optimal position since the actin filaments in the cell cytoskeleton are misaligned and separated from the flat surface. Therefore, it is necessary to measure the cell adhesion forces on the curved surfaces of bones and implants in vivo by using traditional methods as well as novel bio micro and nano electro mechanical systems (bio MEMS/NEMS) force sensors. The studies of material layer and microstructure curvature effects on other cell behaviors will play fundamental roles in cell and tissue engineering. The cell culture experiments and related discussions reported here imply that this class of material layers, micro glass ball embedded gels, can be useful tools to study cell mechanobiological responses to material layer and microstructure curvatures, related cell and tissue engineering researches, and biomedical applications.

Applications of the various embodiments of the present invention are many, including for use in general cell studies as described herein, wherein the invention allows control over the morphology and structure of the resulting cells and tissues. Also, cells can be cultured on material layers and microstructures formed according to the teachings of the present invention. The differentiation and lineage of these cells may be influenced by the curvature of the material layer and the microstructures. Early detection and isolation of cancer cells may also be accomplished by using the teachings of the present invention, which may lead to new strategies and devices for cancer detection and treatment.

Figure 6:
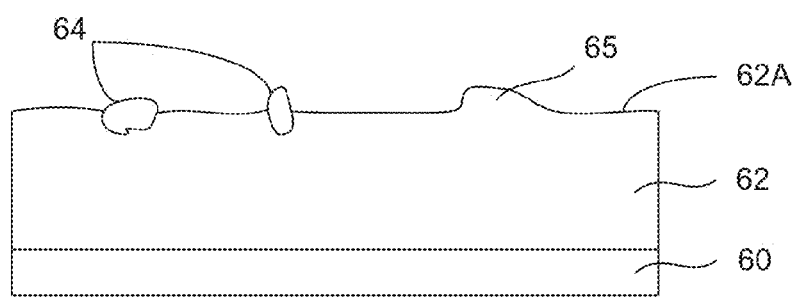
FIG. 6 illustrates microstructures embedded in a material layer.

According to another embodiment, the microstructures comprise the same material as the material layer and emerge or extend from the material layer as shown in FIG. 6 illustrating a substrate 60, a material layer 62 and microstructures 64 comprising the same material as the material layer 62 and emerging or extending from an upper surface 62A of the material layer 62 to form curved structures for cell or tissue culturing or for use in other surface interface applications.

In lieu of microstructures embedded in or extended from the material layer or in addition thereto, FIG. 6 also illustrates another embodiment having a protrusion 65 formed in the material layer 62 and formed of the same material as the material layer 62. Cells or tissues can be cultured on the protrusion 65. The protrusion 65 obviates the need for separate microstructures for culturing tissues or cells or for use in other surface interface applications.

Although in the embodiment of FIG. 6 the microstructures 64 comprise the same material as the material of the material layer 62 such is not required as in other embodiments described herein the material of the microstructures and the material layer are different.

Figure 7:
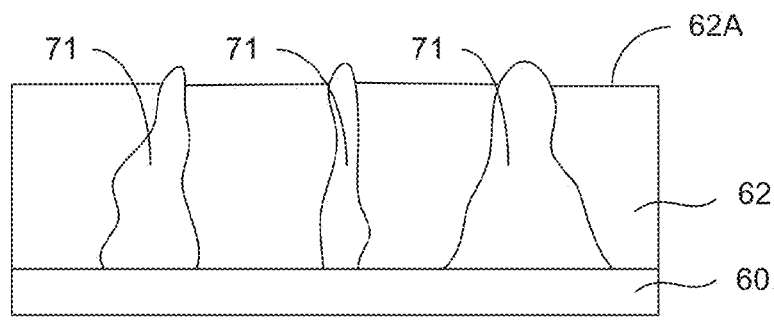
FIG. 7 illustrates microstructures extending through and above a material layer.

In another embodiment illustrated in FIG. 7, a material of microstructures 71 extends from the substrate 60 through the material layer 62 to emerge from the upper surface 62A to present microstructure surfaces for cell and tissue culturing.

In the various embodiments described herein, a stiffness of the microstructures can be greater than, significantly greater than, orders of magnitude greater than, or many orders of magnitude greater than a stiffness of a material layer in which the microstructures are embedded or from which the microstructures extend.

Alternately, in the various embodiments described herein, a stiffness of the microstructures can be smaller than, significantly smaller than, orders of magnitude smaller than, or many orders of magnitude smaller than a stiffness of a material layer in which the microstructures are embedded or from which the microstructures extend.

Figure 8:
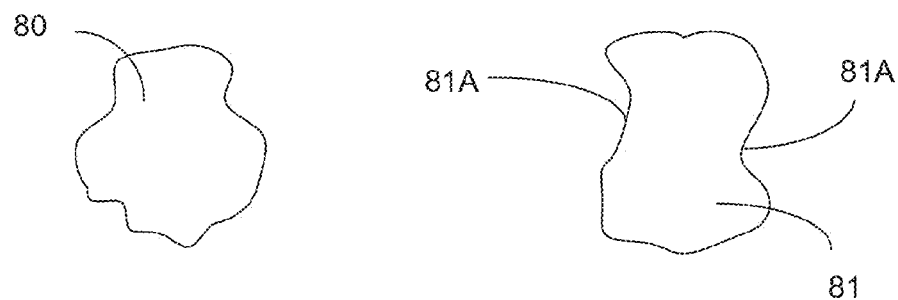
FIGS. 8 and 9 illustrate various curved surfaces on microstructures.

In the certain described and illustrated embodiments the microstructures have been illustrated and described as concave (i.e., having a negative curvature) in shape. This is not necessarily required as convex (i.e., having a positive curvature) microstructure shapes are also useful in cell and tissue culturing. FIG. 8 illustrates a microstructure 80 having a generally convex shape and a microstructure 81 having concave surface regions 81A.

Figure 9:
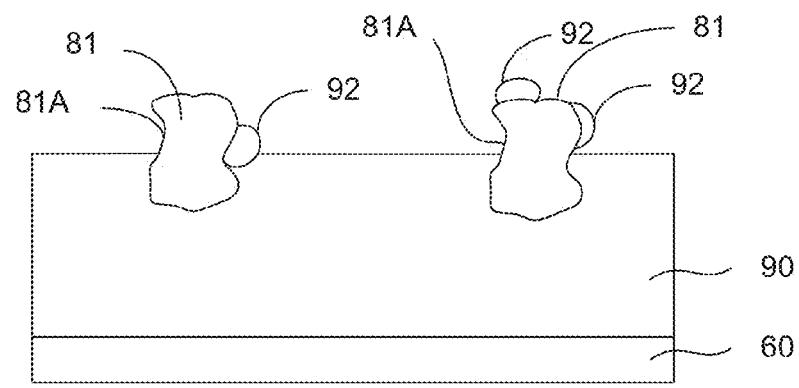

If the microstructure 81 is placed in a material layer 90 as in FIG. 9, the concave surface regions 81A can be filled with any one of several materials 92 having different stiffness values that are either greater or smaller than the stiffness value of the microstructure 81 and/or the stiffness value of the material layer 90. In another embodiment the concave and convex surface regions of the microstructures 81 of FIG. 9 are not filled with material, thereby presenting different shapes for culturing cells and tissues and presenting a single stiffness value of the microstructure 81.

Figure 10:
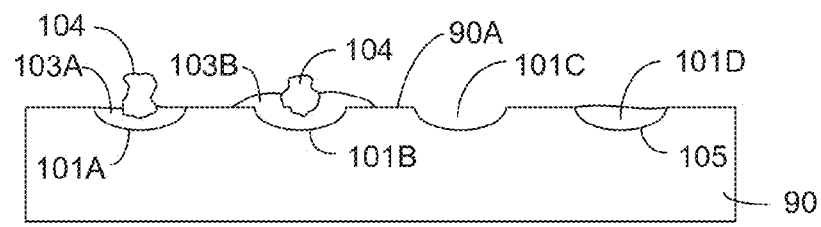
FIG. 10 illustrates microstructures disposed in wells in a material surface.

FIG. 10 illustrates several different embodiments of the present invention. Wells, holes, or pits 101A, 101B, 101C, and 101D (i.e., negatively shaped or concave openings and hereinafter referred to as wells or surface features) are formed in a relatively flat upper surface 90A of the material layer 90.

A gel or another material 103A within the well 101A and a microstructure 104 within the material 103A depict one embodiment of the invention.

According to another embodiment a gel or another material 103B is disposed within the well 101B and also extends onto regions of the upper surface 90A proximate the well 101B. The microstructure 104 is disposed within the gel or other material 103B.

The well 101C is devoid of both any material and a microstructure. Cells and tissues can be cultured in the well 101C.

In yet another embodiment the well 101D is filled with a material 105 that presents a stiffness value (a soft or rigid material or a material having a stiffness value the same as the stiffness value of the material 90). Cells or tissues can be cultured on the material 105 or the material 105 can be used for other interface applications.

The microstructures 104 can be of various stiffness values (greater or, smaller than or equal to the stiffness value of the material layer 90). Also the wells 101A-101D (and the wells presented in other embodiments of the invention) can be randomly or uniformly disposed within the material layer 90 or placed at defined locations or in a pattern within the material layer 90. The wells can be of the same or different sizes (e.g., depth or dimension of the well opening) and of the same or different cross-sectional shapes as illustrated in FIG. 11.

Figure 11:
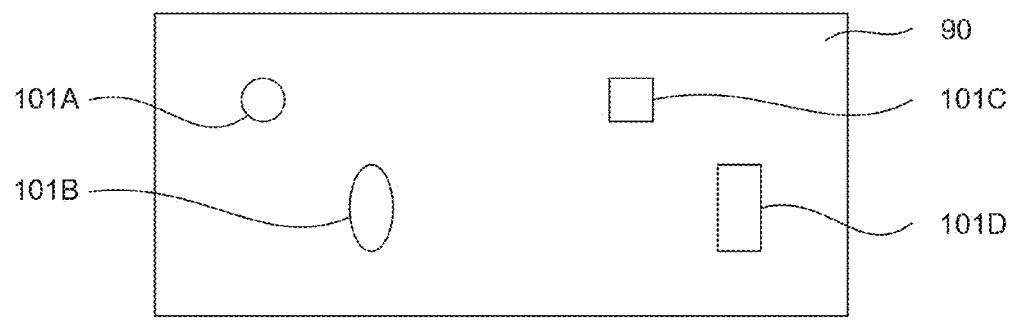
FIG. 11 illustrates different cross-sectional shapes for the wells of FIG. 10.

FIG. 11 depicts a top view of the material layer 90, of FIG. 10 illustrating various exemplary cross-sectional shapes for the wells, including a circular well 101A, an elliptical well 101B, a square well 101C and a rectangular well 101D. The well can also define other cross-sectional shapes dependent on the application.

In one embodiment microstructures for use with various cross-sectionally shaped wells 101A-101D are shaped according to the shape of the well in which the microstructure is disposed (i.e., circular, elliptical, square, or rectangular).

Figure 12:
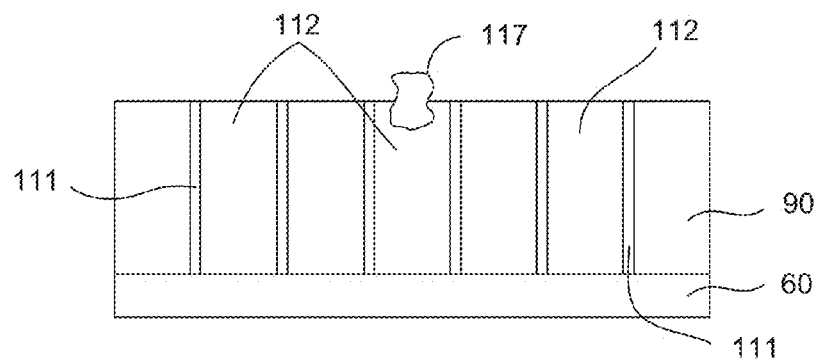
FIGS. 12 and 13 illustrate frame structures in a material layer.

FIG. 12 illustrates frame structures 111 extending upwardly from the substrate 60 to partition the material layer 90 into regions 112. A microstructure 117 is disposed within one of the regions 112.

Figure 13:
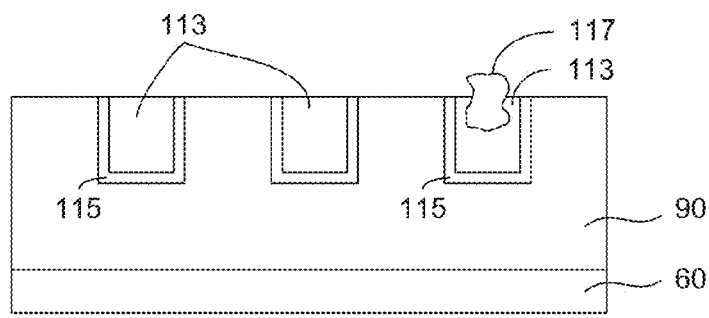

In FIG. 13 frame structures 115 are suspended within the material layer 90 and in effect form wells 113. The microstructure 117 is disposed within one of the wells 113.

Figure 14:
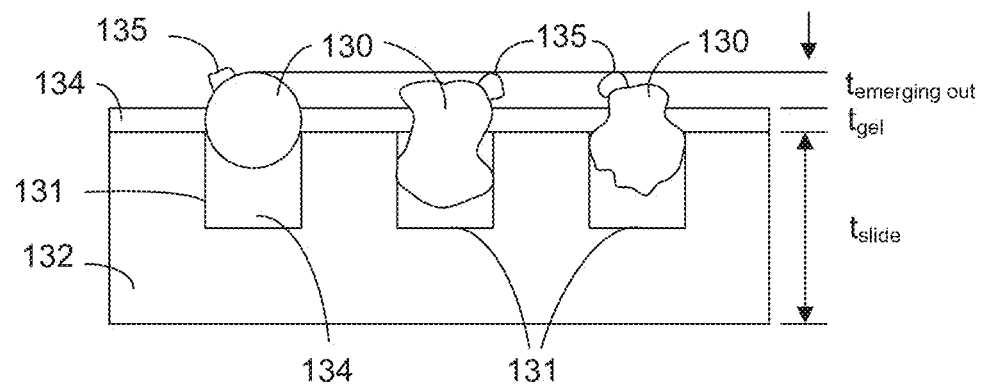
FIGS. 14, 15 and 16 illustrate microstructure disposed in wells in a material layer.

FIG. 14 illustrates a front view of micro glass balls embedded in a PA gel for systematically studying cellular responses to substrate curvatures, local substrate curvatures and substrate curvature patterns, and local substrate stiffness and substrate stiffness patterns. For example in one embodiment the glass slide 132 of FIG. 14 is made of a photo-structurable APEX™ glass of Life Bioscience, Inc. of Albuquerque, N.M. (LBSI), and in one embodiment a thickness of the slide ($t_{slide}$) is 1 millimeter. A top surface of the glass slide 132 is fabricated to form wells 131 and well arrays.

Glass balls or microstructures 130 are disposed in the wells to form desired patterns of balls. A layer of PA gel 134 or another suitable material is formed on top of the slide 132 (and within the wells in one embodiment) to provide a desired substrate stiffness, to prevent rolling of the balls, and to achieve a desired emerging-out height ($t_{emerging-out}$) of the balls from the gel surface.

One exemplary fabrication process for the above-referenced glass slide 132 proceeds as follows:

Step 1: Make a quartz-chrome mask with the clear (transparent) regions showing the distribution of the wells 131 to be fabricated on the top surface of the glass slide.

Step 2: Expose the APEX™ glass slide to 310 nanometer mid-ultraviolet light by using direct contact with the quartz-chrome mask.

Step 3: Bake the exposed APEX™ glass slide in the following two steps.
  1. The temperature is raised to 500° C. at a ramp rate of 6° C./min and held there for 75 minutes to allow the photo-activators, created during the exposure process, to migrate together forming nano-clusters.
  2. The temperature is raised to a second temperature, 575° C., at a ramp rate of 3° C./min and held there for 75 minutes to induce ceramic nucleation within the glass matrix around the previously formed nano-clusters.

Step 4: Etch the baked glass slide in a hydrofluoric acid (HF) solution in an ultrasonic bath creating the micro wells.

The desired depth of the wells 131 can be controlled by varying etch concentrations and etch times. For initial processing protocols, the 10:1 (water: 49% HF) mixtures can be used as the etching HF solution.

Depending on the desired thickness of the gel 134 ($t_{gel}$) on the top surface of the fabricated glass slide 132, an appropriate volume of the PA solution with the polymerizing agents is placed on top of the fabricated glass slide, and glass balls of various diameters are immediately dropped onto the PA solution. To fit the balls 130 into the wells on the slide surface, a regular cover slip is carefully placed on top of the balls and the PA solution to gently push and press the balls so that the balls move into the wells. After the polymerization process of the PA solution is complete the cover slip is slowly peeled off to expose the balls 130 and PA gel surface 134.

According to this preparation process, the function of the micro wells fabricated on the glass slide is to position the micro glass balls to form desired patterns of balls, and therefore, the depth of the wells is initially and conveniently chosen, in one embodiment, as half of the thickness of the slide, i.e., 0.5 millimeters. The diameter of the wells is initially determined by the requirement, in one embodiment, that after a ball fits into a well the lowest point of the ball is at least 0.2 millimeters from the bottom of the well. The empty space of the well under the ball can also be filled with the gel material 134 (as shown in FIG. 14) according to the platform preparation process.

Besides providing a desired substrate stiffness on top of the slide for cell culturing, the PA gel material in the platform prevents rolling of the balls and realizes a desired emerging-out height ($t_{emerging-out}$) for the balls. In one embodiment a diameter of the balls can vary from about 5 microns to about 6 millimeters. Also, by varying the concentrations of acrylamide and bis-acrylamide in the PA solution, the Young's modulus (E) of the PA gel can be varied to cover the entire span of tissue-level elasticity.

With reference to FIG. 14, cells or other tissues 135 are cultured on an exposed surface of the balls 130. The location of each well 131 is selected to present a desired uniform or random pattern for culturing of the cells or tissues 135.

Figure 15:
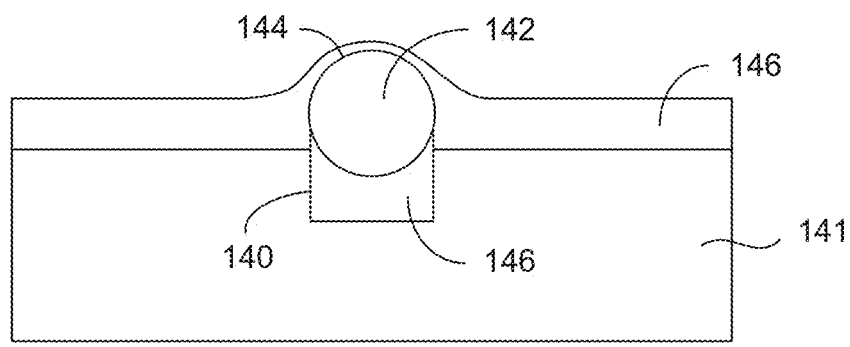

FIG. 15 illustrates yet another embodiment for presenting local curvatures and curvature patterns for use in cell and tissue culturing and other surface interface applications. A well 140 is defined in a material layer 141. A microstructure 142, such as, but not limited to a glass ball, is disposed within the well 140 and a cell 144 grows on a surface of the microstructure 142. A gel or another relatively soft or rigid material 146 is disposed within the well 140 and atop the material layer 141 to present a curvature (and stiffness) differentiation between the microstructure 142 and the material 146.

Figure 16:
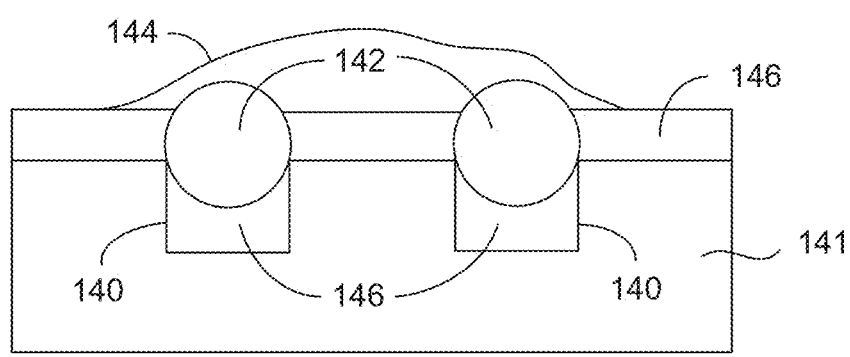

The embodiment of FIG. 16 is similar to the embodiment of FIG. 15 but depicts two wells 140, two microstructures 142, and the cell 144 extending over both microstructures 142.

Figure 17:
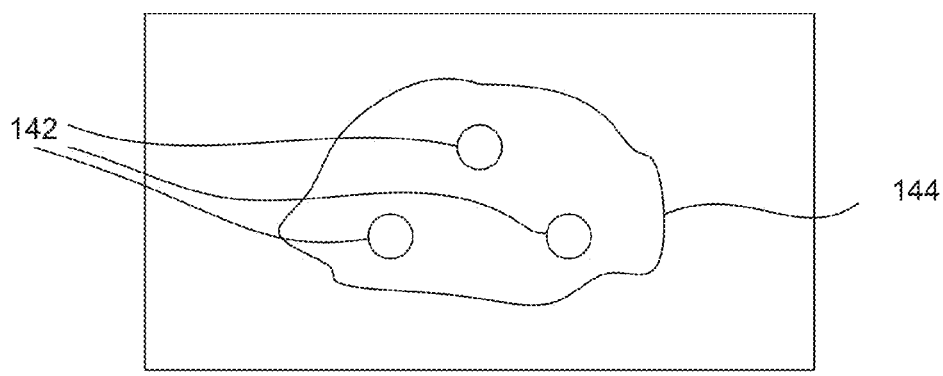
FIGS. 17 and 18 illustrate top views of well configurations.
Figure 18:
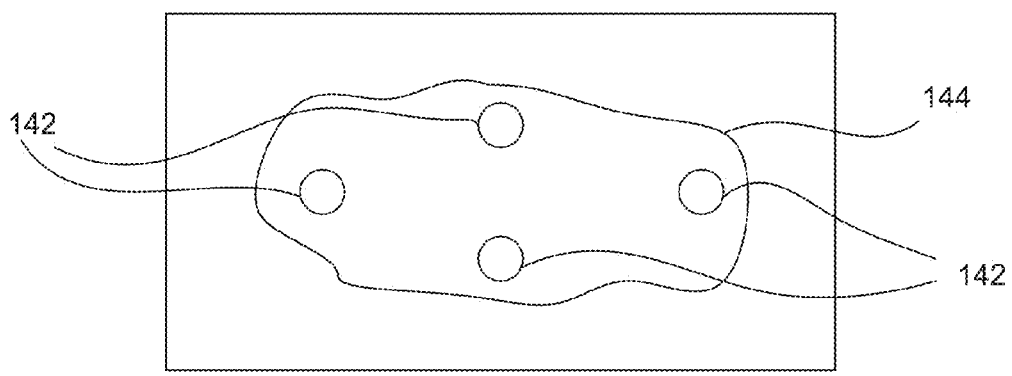

FIGS. 17 and 18 are top views illustrating two possible arrangements for the microstructures. FIG. 17 depicts three microstructures 142 and FIG. 18 depicts four microstructures 142. The cell or tissue 144 grows over both clusters of the microstructures.

The patterns of the microstructures (and their corresponding wells) of FIGS. 17 and 18, that is, the stiffness patterns of FIGS. 17 and 18, are merely exemplary. Other stiffness and curvature patterns, as determined by the material and location of the microstructures, can be used based on the application.

Figure 19:
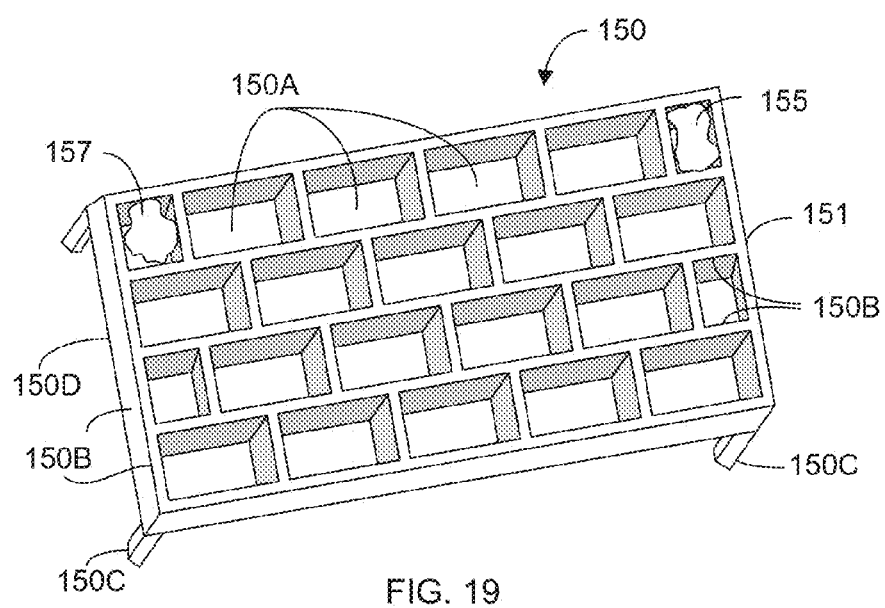
FIGS. 19, 20 and 21 illustrate different frame structures for use with the present invention.

FIG. 19 illustrates a frame 150 fabricated, in one embodiment, from single-crystal silicon using a modified single-crystal reactive etching and metallization (SCREAM) process, which is known in the art. Various semiconductor and MEMS processes can also be used to form the frame 150.

The frame 150 can also be fabricated by a process described in a paper entitled "Micromachined Force Sensors for the Study of Cell Mechanics", by Shengyuan Yang (the present inventor) and Taher Saif, Review of Scientific Instruments 76, 044301 (2005); doi: 10.1063/1.1863792, which is also incorporated by reference.

The frame 150 comprises a border 151 bounding a plurality of rectangular openings 150A separated by upstanding wall surfaces 150B. Other frames of different sizes, geometries, opening shapes, overall shapes, compartment or opening patterns, compartment wall thicknesses, and compartment shapes (i.e., any closed polygonal shape) and sizes, and wall patterns can be used according to the present invention. These frame parameters can be selected according to the requirements of the cell and tissue growth experiments. For example, although the frame openings 150A are illustrated as uniformly distributed and rectangular in shape in FIG. 19, such is not required and may not be desired for studying certain cell and tissue cultures. The frame 150 is supported by legs 150C.

In one embodiment, the thickness of the silicon structures of the frame 150 can be reduced by forming silicon dioxide ($SiO_2$) by thermal oxidation of the silicon, followed by hydrofluoride (HF) etching of the $SiO_2$. Using this technique (or another semiconductor processing or MEMS processing techniques) frame structures with desired stiffness patterns at micrometer and nanometer scales can be obtained.

The frame 150 illustrated in FIG. 19 can be formed from a material having any stiffness value (e.g., silicon can be used for a relatively high-stiffness value) and the openings 150A filled with a material 155 having a different stiffness value than the stiffness value of the frame 150. The material 155 can be injected or dispensed into the openings 150A or the frame 150 can be immersed into the material 155 such that the material 155 fills the openings 150A. The material 155 may comprises a low stiffness polyacrylamide gel or another material having a different stiffness value than the stiffness value of the frame 150. For example, a material having a higher stiffness value than the stiffness value of the frame 150 can be disposed within the openings 150A. The material 155 within any of the openings 150A can present any of the various properties and shapes described herein, such as any stiffness value, shaped to form protrusions or wells, as depicted in respective FIGS. 6 and 10.

In another embodiment the material 155 within one or more of the openings 150A serves as a support for a microstructure 157, having a different stiffness value than the stiffness value of the frame 150 and/or the material 155. The microstructure 157 can present any of the various properties described herein, such as the concave and convex shapes illustrated in FIG. 8.

Figure 20:
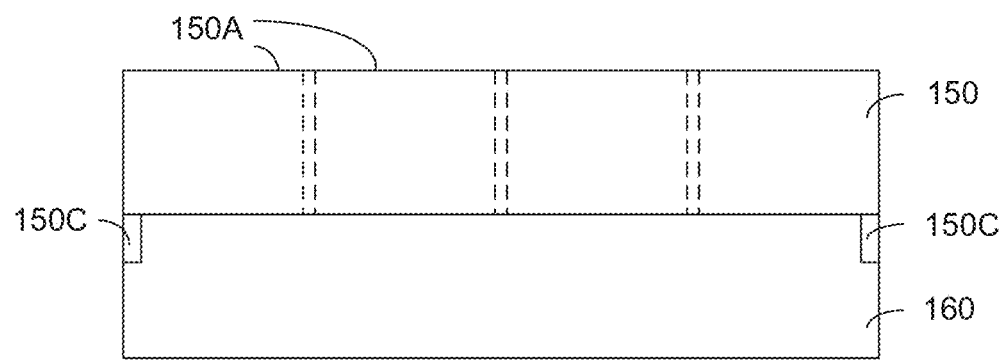
Figure 21:
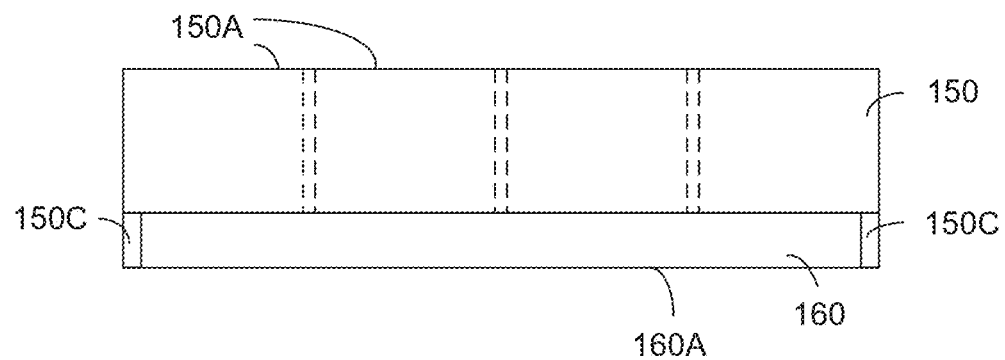

The frame 150 can be suspended within a material 160, which may comprise a gel, as shown in FIG. 20. In another embodiment as illustrated in FIG. 21, the frame 150 is disposed within the material 160 such that the legs 150C extend to a bottom surface 160A of the material 160.

Polydimethylsiloxane (PDMS) (a material having a high value of Young's modulus) can also be used to fabricate the frame 150. Since the Young's modulus of PDMS can be varied from tens of kPa to 2.5 MPa or higher and PDMS structures down to 1 to 2 micrometers can be fabricated, PDMS frames may be preferable to silicon frames for use in certain applications. The modulus can be varied by changing the concentration of the various constituent elements or by changing the constituent elements of the PDMS.

The polyacrylamide-silicon gel that may comprise the material 155 (see FIG. 19) or may be used for filling the openings 150A and in which the microstructure 157 may be disposed, can be prepared according to either of the following two methods.

Method 1:
1) Place sterilized cover glass on bottom of Petri dish.
2) Place silicon frame on top of cover glass.
3) Mix 40 g of acrylamide powder to 100 ml of de-ionized water to create 40% w/v solution.
4) Mix 2 g of bisacrylamide powder to 100 ml of de-ionized water to create 2% w/v solution.
5) Pipette 1000 ul of acrylamide solution, 200 ul of bisacrylamide solution, 50 ul of 1M HEPES (4-(2-hydroxyethyl)-1-piperazineethanesulfonic acid) solution and 3750 ul of de-ionized water into a beaker and mix thoroughly.
6) Degas the solution for 20 minutes to remove oxygen which inhibits polymerization.
7) Add 1 g of ammonium persulfate to 10 ml of de-ionized water to create 10% w/v solution.
8) Pipette 20 ul of ammonium persulfate solution and 20 ul of TEMED (Tetramethylethylenediamine) into beaker and swirl gently.
9) Immediately pipette 25 ul of the final solution onto silicone substrate (i.e., the frame 40 of FIG. 2) evenly and place a cover glass on top. Apply a downward pressure to the over glass to ensure that the cover glass rests on top of the silicon substrate.
10) Let solution polymerize for 30 minutes.
11) Rinse substrate with PBS (Phosphate Buffered Saline) and gently remove the cover glass.

Method 2:
1) Put sterilized cover glass on bottom of Petri dish.
2) Mix 40 g of acrylamide powder to 100 ml of de-ionized water to create 40% w/v solution.

3) Mix 2 g of bisacrylamide powder to 100 ml of de-ionized water to create 2% w/v solution.

4) Pipette 1000 ul of acrylamide solution, 200 ul of bisacrylamide solution, 50 ul of 1M HEPES (4-(2-hydroxyethyl)-1-piperazineethanesulfonic acid) solution and 3750 ul of de-ionized water into a beaker and mix thoroughly.

5) Degas the solution for 20 minutes to remove oxygen which inhibits polymerization.

6) Add 1 g of ammonium persulfate to 10 ml of de-ionized water to create 10% w/v solution.

7) Pipette 20 ul of ammonium persulfate solution and 20ul of TEMED(Tetramethylethylenediamine) into beaker and swirl gently.

8) Immediately pipette 25 ul of the final solution onto the cover glass evenly and place the frame 40 on the final solution. Apply downward pressure to the frame using another cover glass so that the frame rests on top of the cover glass and does not float on the solution.

9) Let the solution polymerize for about 30 minutes.

10) Rinse substrate with PBS (Phosphate Buffered Saline) and remove cover glass gently.

It is well-known that substrate stiffness directs cell lineage specification, but the conclusion is based on the experimental observations from cells growing on substrates of uniform stiffness. In one embodiment of the present invention the microstructures are in the form of micro glass balls embedded within a PA gel. The glass balls are infinitely stiff compared to the soft PA gel (since the glass ball material has an infinitely-large Young's modulus compared to the PA gel material). Therefore, the glass balls embedded in the gel locally enhance the stiffness of the gel creating a unique and flexible class of substrates with non-uniform stiffness for cell and tissue culturing.

This locally enhanced substrate stiffness promotes fibroblast spreading on soft PA gels. In this embodiment the locally enhanced substrate stiffness is referred to as a local substrate stiffness, and the patterns formed by local substrate stiffness are called substrate stiffness patterns. The structures of this embodiment can be used to study the differentiation responses of cells to local substrate stiffness and substrate stiffness patterns created by embedded micro glass balls or another microstructure.

Figure 22:
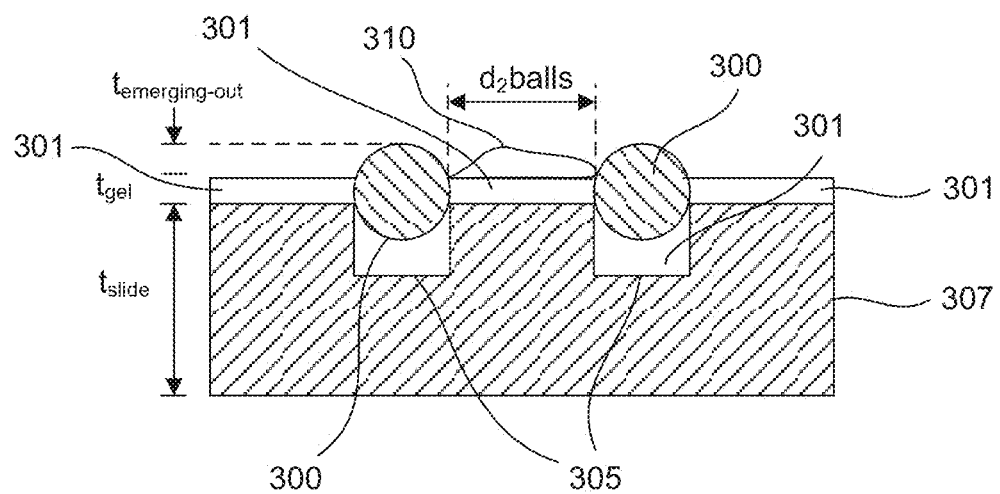
FIGS. 22, 23 and 24 illustrate, respectively, a side view and two top views of microstructures disposed in wells in a material layer.
Figure 23:
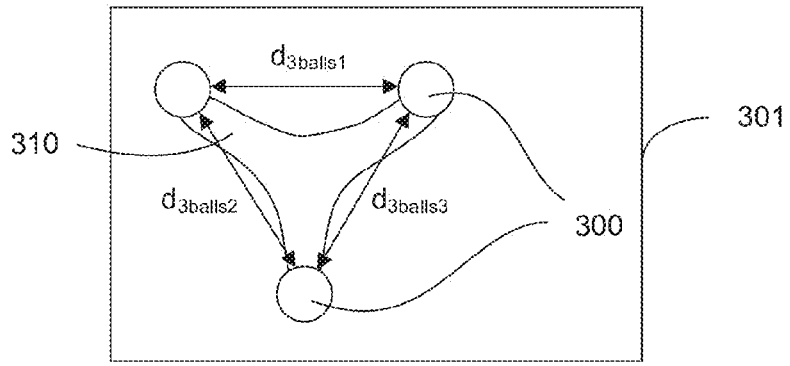
Figure 24:
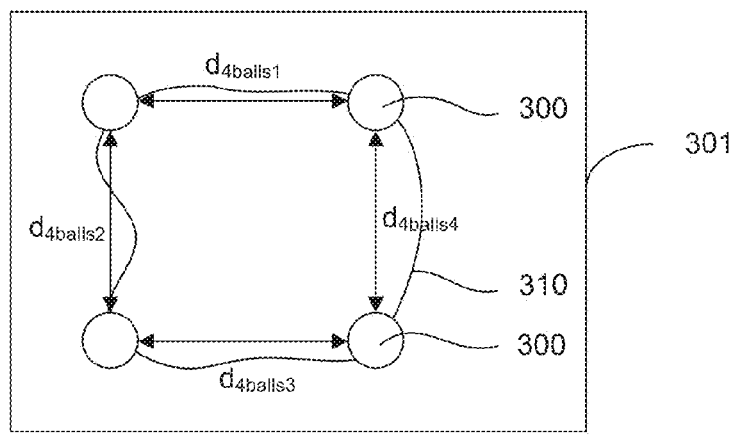

FIGS. 22, 23 and 24 illustrate embodiments for use studying the differentiation responses of cells (e.g., stem cells) to local substrate stiffness and substrate stiffness patterns by using micro glass balls 300 embedded in a gel 301. According to one embodiment 5 to 50 µm micro glass balls 300 are disposed in corresponding 5 to 50 µm micro wells 305 on a glass slide 307 as illustrated in FIG. 22. These dimensional ranges are merely exemplary as other dimensions for the micro glass balls and wells can be used. Also, a location of the micro wells 305 can be random, or uniform, or the micro wells can be positioned to form a desired pattern.

The various dimensions are as indicated and additionally a diameter of the glass balls 300 is denoted $D_{ball}$ and the diameter of the wells 305 is denoted $D_{well}$. The dimensions can be varied based on the application.

The distance between the micro glass balls in FIGS. 22, 23 and 24 are on the order of about 1 nanometer to about 10 millimeters so that a cell 310 may grow between the balls 300. FIG. 22 shows the cell 310 growing between and spreading (stretched) to two adjacent glass balls 300. The parameters $t_{emerging-out}$, and $D_{ball}$, and the distance between the two balls ($d_{2balls}$) can be varied as desired to study the differentiation responses of the cell 310 to local substrate stiffness and substrate stiffness patterns.

The top view of FIG. 23 shows the cell 310 growing between and spreading (stretched) to three adjacent glass balls 300. The dimensions $t_{emerging-out}$, $D_{ball}$, and the three distances ($d_{3balls1}$, $d_{3balls2}$, and $d_{3balls3}$) between any two of the three balls can be controlled to study the differentiation responses of the cell to local substrate stiffness and substrate stiffness patterns.

The top view of FIG. 24 shows the cell 310 growing between and spreading (stretched) to four adjacent glass balls 300. The dimensions $t_{emerging-out}$, $D_{ball}$, and the four distances ($d_{4balls1}$, $d_{4balls2}$, $d_{4balls3}$, and $d_{4balls4}$) between any two balls on the four sides of the quadrilateral formed by the four balls can be controlled or varied to study the differentiation responses of the cell to local substrate stiffness and substrate stiffness patterns.

Various values of local substrate stiffness, substrate stiffness patterns, dimensions and other controllable parameters can be utilized according to different embodiments and applications.

Figure 25:
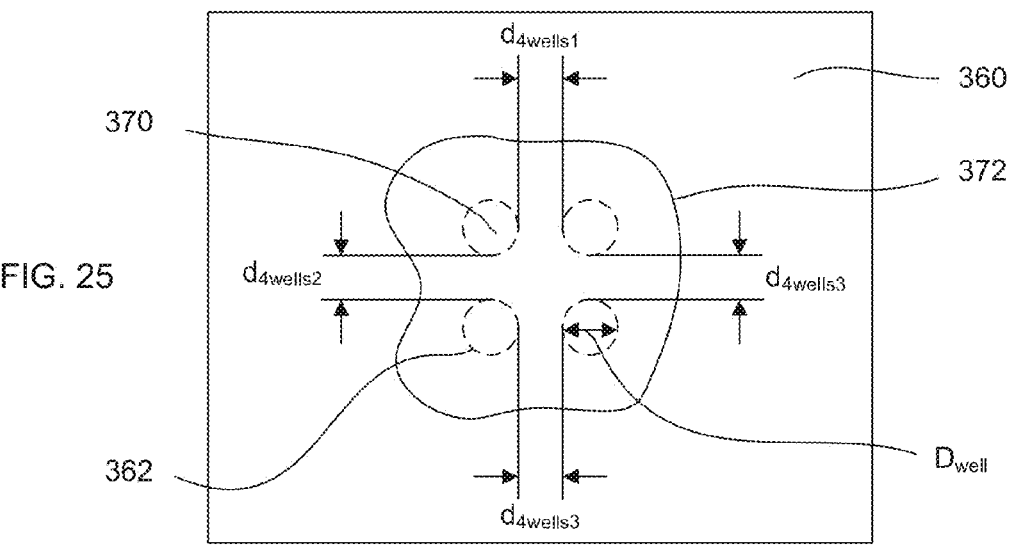
FIGS. 25 and 26 illustrate, respectively, a top and a side view of a material layer comprising pillars formed therein.
Figure 26:
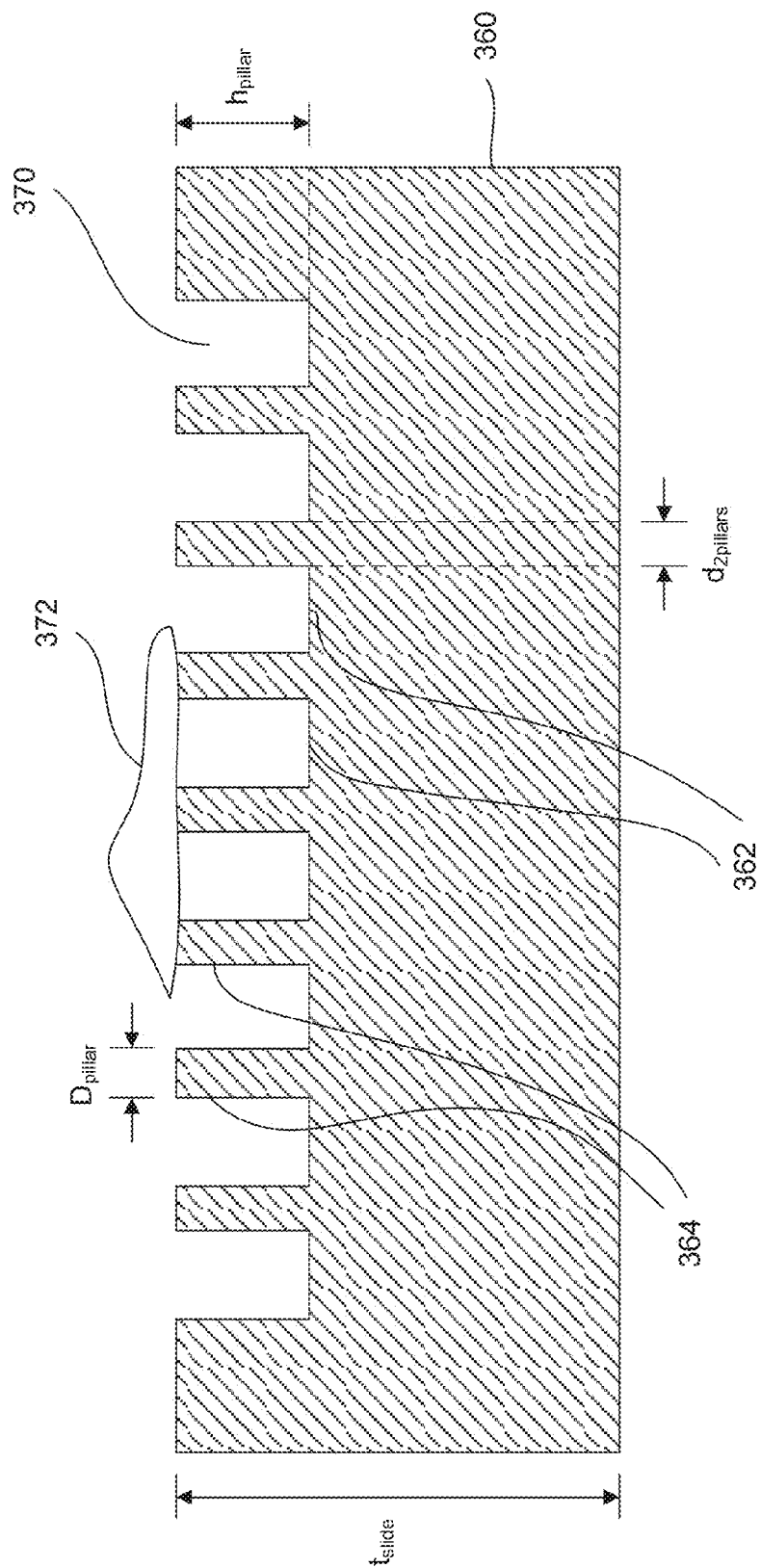

FIG. 25 is a top view and FIG. 26 a side view illustrating a glass slide 360 defining wells 362 and pillars 364 fabricated on a top surface 360A of the glass slide 360. PA gel 370 is disposed within wells 362 (i.e., the spaces between the pillars 364). A cell 372 (e.g., a stem cell) grows across one or more wells 362 and pillars 364.

The structure of FIG. 26 presents a unique and flexible flat non-uniform substrate for cell and tissue cultures. Note that the curvature effects on cell and tissue behaviors are not involved in this embodiment. The flat surfaces of these composites, i.e., these substrates formed by wells 362 and pillars 364 with the gel 370, provide flat local substrate stiffness and substrate stiffness patterns for cell studies. The gel 370 fills the wells 362 to provide a locally soft substrate stiffness, and the pillars 364 provide locally-rigid substrate stiffness. This structure can be used to study the differentiation responses of cells to both the single local substrate stiffness, provided by the gel in a single well or by a single pillar surrounded by a gel material, and the substrate stiffness patterns formed by the single local substrate stiffness.

If a cell growing on the structure of FIGS. 25 and 26 covers only one well 362 filled by gel material 370 and the top surfaces of the surrounding pillars 364, then the cell responses to this single locally-soft substrate stiffness can be studied.

If a cell growing on the structure of FIGS. 25 and 26 covers only one pillar 364 and its surrounding gel material 370, then the cell responses to this single locally-rigid substrate stiffness can be studied.

If a cell growing on the structure of FIGS. 25 and 26 covers two or more wells 362 filled by gel material 370 and the top surface of the surrounding pillars 364 or covers two or more pillars 364 and their surrounding gel materials 370, then the cell responses to this substrate stiffness pattern can be studied.

FIGS. 25 and 26 show the various dimensions that can be varied according to the intended application and also show two exemplary structures for use in studying the differentiation responses of cells to local substrate stiffness and substrate stiffness patterns as created by the array of the wells 362 and the array of the pillars 364.

FIG. 25 is a top view of the cell 372 growing on four adjacent PA gel-filled wells 362. In one embodiment the diameter and depth of each well is from about 5 to 100 µm.

FIG. 26 is a frontal sectional view of the cell 372 growing on a array of glass pillars 364 and the surrounding PA gel material 370 within the wells 362. The diameter of a pillar, $D_{pillar}$, the distance between two adjacent pillars, $d_{2pillars}$, and the height of each pillar, $h_{pillar}$, can all be varied from about 5 to 100 μm. Various numerical combinations between the diameter and depth of each well and between the diameter and height of each pillar and distance between two adjacent pillars can be employed to determine response of the cell to these various dimensions.

Although typical values for the sizes or dimensions of the microstructures have been set forth herein, in fact the size or dimensions can vary as required for culturing cells and tissues and in other surface and interface applications.

In an embodiment where the microstructure and the material layer comprise different materials the apparatus may be considered a composite apparatus or a composite structure.

Although the structures on which the cells and tissues are cultured according to the present invention are generally referred to herein as microstructures, the term is intended to encompass structures of both the nano-scale and micro-scale size ranges, generally encompassing a range from about 1 nanometer to about 10 millimeters.

The materials, shapes, sizes, stiffness, and curvatures of the microstructures and material layers described herein can take any value (i.e., the same or different values) and further can be uniform or non uniform. The stiffness of the microstructures can be larger or smaller than the stiffness of the material layer. Certain embodiments employ rigid glass balls as the microstructures and other embodiments employ relatively soft microstructures. The microstructures may comprise cylinders, balls, shells or any other shape as desired for the application. Also, the material, stiffness, and curvatures of the microstructures can be the same or different from the material, stiffness and the curvature of the material layer. The properties of the microstructures and the material layer can be uniform or non-uniform and can have any pattern, e.g., either a random pattern or a defined pattern. The local shapes or curvatures on the surface of the microstructures and the material layer as described in the various embodiments can be convex (positive) or concave (negative)

Figure 27:
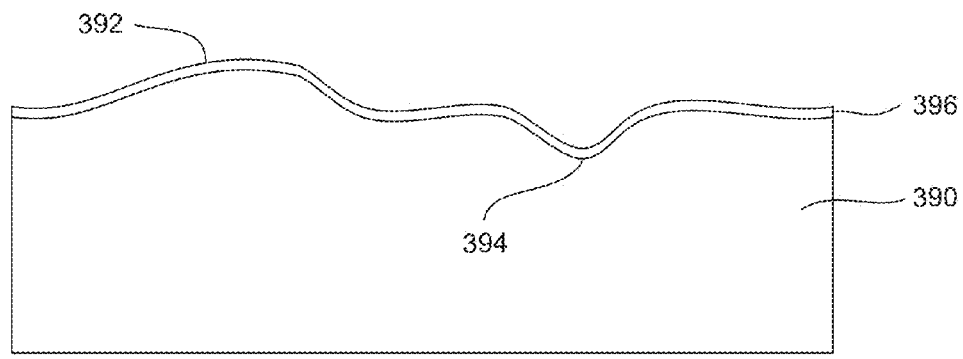
FIGS. 27 and 28 illustrate a material layers with various shapes and features formed therein.

Certain of the embodiments described comprise a material layer with protrusions (see FIG. 6 for example) and with wells (see FIG. 10 for example). In another embodiment the material layer (with or without protrusions or wells) is covered with a gel-like material or another material on which cells and tissues can be cultured. See FIG. 27 where a material layer 390 comprises a protrusion 392, a well 394 and a flat region 395. A gel-like material 396 is disposed over the protrusion 392, the well 394 and the flat region 395. No microstructures are present in this embodiment.

Figure 28:
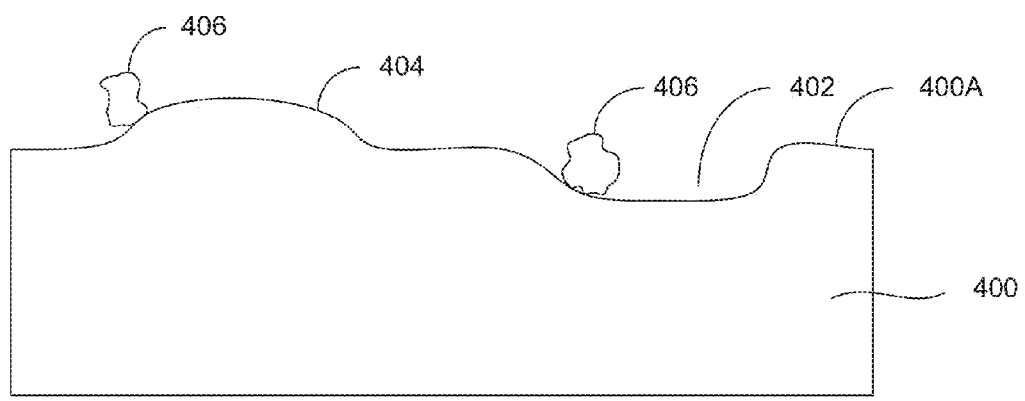

FIG. 28 illustrates a material layer 400 having an upper surface 400A that presents a concave region 402 and a convex region 404 for use in cell and tissue culturing (as represented by microstructures 406) or for use in other surface interface applications. As can be appreciated by those skilled in the art, a single material layer may comprise only a convex surface, only a concave surface, or a both a convex and a concave surfaces in different regions of the material layer.

The various described embodiments present curvature and stiffness arrangements (e.g., substrate curvatures, local substrate curvatures, substrate curvature patterns, local substrate stiffness and substrate stiffness patterns) for cell and tissue culturing and for other surface interface applications. As can be appreciated from the foregoing description of the various embodiments of the inventions, when a cell grows on a single microstructure or on two or more microstructures (for example as illustrated in FIG. 14 as well as many other figures of the present application), this configuration allows one to conveniently study the cell response to substrate curvatures, local substrate curvatures and substrate curvature patterns. When a cell grows between two or more microstructures (for example as illustrated in FIG. 22), this configuration allows one to conveniently study the cell response to local substrate stiffness and substrate stiffness patterns.

It is to be understood that the above-described arrangements of well, microstructures, micro wells, etc. are merely illustrative of the many possible specific embodiments that can be devised to represent application of the principles of the invention. Numerous and varied other arrangements can be devised in accordance with these principles by those skilled in the art without departing from the spirit and scope of the invention.

What is claimed is:

1. A structure for use in cell and tissue culturing and surface and interface applications, the structure comprising:
a first material layer; microstructures partially embedded and immoveable within the first material layer, each microstructure presenting a curvature value and a stiffness value of an exposed region protruding above an upper surface of the first material layer, wherein a curvature value and a stiffness value of at least two microstructures are different and a curvature value and a stiffness value of at least one microstructure is different from a curvature value and a stiffness value of the first material layer;
wherein a size of each microstructure is between one nanometer and ten millimeters;
a material of the first material layer and a material of the microstructures comprising glass, silicon, silicon nitride, silica, plastic, or gel, and wherein a material of each microstructure is the same as or different from a material of another microstructure and a material of the first material layer; and
the structure for use in studying cell responses to curvatures, local curvatures, curvature patterns, stiffness, local stiffness, and stiffness patterns when a cell grows on one or more of the microstructures, the first material layer, or between two or more of the microstructures.

2. The structure of claim 1 wherein a shape of a one or more of the microstructures comprises a ball-like, spherical, elliptical, cylindrical, square, or rectangular, and the curvature of the exposed region of one or more of the microstructures comprises a concave curved surface or a convex curved surface.

3. The structure of claim 1 further comprising one or more wells or protrusions in or on the first material layer, the one or more wells or protrusions disposed randomly or in a pattern and having the same or different materials, sizes, stiffness values, and cross-sectional shapes relative to each other, and having the same or different materials relative to a material of the first material layer, wherein the cross-sectional shapes comprise a circular, elliptical, square, or rectangular cross-sectional shape, and wherein one or more of the microstructures are disposed in or on one or more of the wells or protrusions with an exposed region of the one or more microstructures protruding above an upper surface of the first material layer.

4. The structure of claim 3 wherein the one or more wells or protrusions extend through at least a portion of the first material layer.

5. The structure of claim 3 further comprising a second material layer disposed in or on the one or more of the wells or protrusions and disposed on one or more regions of the first material layer between two or more of the wells or protrusions to fix one or more of the microstructures within or on the one or more of the wells or protrusions a material of the second material layer comprising a gel, plastic, silica, glass, silicon, or silicon nitride.

6. The structure of claim 5 wherein a stiffness pattern of the structure is due to a stiffness value or stiffness values of the second material layer, stiffness values of the one or more of the microstructures, and locations of the microstructures within the second material layer, and a curvature pattern of the structure is due to a curvature or curvatures of the second material layer, curvatures of the microstructures disposed in or on one or more of the wells protrusions and locations of the microstructures disposed in or on one or more of the wells or protrusions.

7. The structure of claim 5 wherein a material of the second material layer, and a material of one or more of the microstructures exhibit the same or different stiffness values and comprise the same material or different materials, the material of the second material layer and a material of one or more of the microstructures each comprising a gel, plastic, silica, glass, silicon, or silicon nitride.

8. The structure of claim 5 wherein the second material layer presents no, one, or more of a concave region, a convex region, a protrusion, or a well.

9. The structure of claim 5 further comprising a third material layer disposed on a surface of one or more of the first material layer, the second material layer, and one or more of the microstructures to form curvatures, local curvatures, and curvature patterns, and to form stiffness, local stiffness, and stiffness patterns.

10. The structure of claim 5 further comprising a cell adhesion protein disposed on any part or parts of at least one of the first material layer, the second material layer, and one or more of the microstructures to promote adhesion of cells and tissues thereon.

11. The structure of claim 1 wherein one or more of the microstructures extends from a lower surface of the first material layer, through the first material layer and above an upper surface of the first material layer.

12. The structure of claim 1 the first material layer presenting none, one, or more concave regions, convex regions, protrusions, or wells therein.

\* \* \* \* \*